United States Patent
McStay et al.

(10) Patent No.: US 8,017,928 B2
(45) Date of Patent: Sep. 13, 2011

(54) LED FLUOROMETER WITH REMOTE DETECTION CAPABILITY

(75) Inventors: Daniel McStay, Banchory (GB); Anton Forte, Greyabbey (GB); Khalid Thabeth, Newtownabbey (GB); Terrence Greenaway, Belfast (GB)

(73) Assignee: Advanced Sensors Limited, Carrickfergus (GB)

(*) Notice: Subject to any disclaimer, the term of this patent is extended or adjusted under 35 U.S.C. 154(b) by 0 days.

(21) Appl. No.: 10/591,611

(22) PCT Filed: Mar. 2, 2005
(Under 37 CFR 1.47)

(86) PCT No.: PCT/EP2005/002270
§ 371 (c)(1),
(2), (4) Date: Oct. 15, 2006

(87) PCT Pub. No.: WO2006/007883
PCT Pub. Date: Jan. 26, 2006

(65) Prior Publication Data
US 2008/0203332 A1    Aug. 28, 2008

(30) Foreign Application Priority Data
Mar. 5, 2004  (GB) .................................. 0404982.1

(51) Int. Cl.
G01V 8/00 (2006.01)
G01J 1/58 (2006.01)
(52) U.S. Cl. .................... 250/559.4; 250/458.1
(58) Field of Classification Search ............... 250/458.1, 250/200, 459.1, 461.1, 552, 553, 253, 226, 250/559.42, 559.4, 559.43, 221; 356/317, 356/311, 319, 323, 416, 417, 419, 420, 425; 422/82.08; 340/539.26, 573.6, 540, 600, 340/605, 612, 618; 73/40.7
See application file for complete search history.

(56) References Cited

U.S. PATENT DOCUMENTS

| | | | | |
|---|---|---|---|---|
| 3,554,653 A | * | 1/1971 | Zielke et al. | 356/153 |
| 3,666,945 A | * | 5/1972 | Frungel et al. | 250/365 |
| 3,996,476 A | * | 12/1976 | Lazzara | 250/559.4 |
| 4,005,605 A | * | 2/1977 | Michael | 374/129 |
| 4,394,573 A | * | 7/1983 | Correa et al. | 250/253 |
| 4,496,839 A | * | 1/1985 | Bernstein et al. | 250/341.6 |
| 4,517,458 A | * | 5/1985 | Barringer | 250/253 |
| 4,771,629 A | * | 9/1988 | Carlson et al. | 73/23.35 |

(Continued)

FOREIGN PATENT DOCUMENTS

JP            04237114 A  *  8/1992

(Continued)

*Primary Examiner* — Que T Le
*Assistant Examiner* — Jennifer Bennett
(74) *Attorney, Agent, or Firm* — The Nath Law Group; Jerald L. Meyer; Jiaxiao Zhang

(57) ABSTRACT

A fluorometer comprising an excitation system including an excitation source for producing excitation light capable of causing fluorescence in fluorescent material; and a detection system for detecting said fluorescence. The excitation source comprises one or more light emitting diodes (LEDs) associated with means for causing said excitation light to form a beam that projects, during use, from the fluorometer. In one embodiment, the excitation system and the detection system are located in respective separate housings, the angular disposition between the housings being adjustable. In other embodiments, the excitation system and the detection system are located in the same housing. The fluorometer is particularly suited for use in detecting leaks in aqueous environments, especially when mounted on an underwater vehicle.

37 Claims, 4 Drawing Sheets

U.S. PATENT DOCUMENTS

| | | | | | |
|---|---|---|---|---|---|
| 4,983,846 | A | * | 1/1991 | Rios et al. | 250/458.1 |
| 5,947,051 | A | * | 9/1999 | Geiger | 114/313 |
| 6,121,053 | A | * | 9/2000 | Kolber et al. | 436/172 |
| 6,157,033 | A | * | 12/2000 | Chudnovsky | 250/338.5 |
| 6,372,895 | B1 | * | 4/2002 | Bentsen et al. | 536/4.1 |
| 6,858,846 | B2 | * | 2/2005 | Hjertman et al. | 250/341.1 |
| 2005/0020926 | A1 | * | 1/2005 | Wiklof et al. | 600/476 |
| 2005/0098713 | A1 | * | 5/2005 | Holland | 250/221 |
| 2005/0174793 | A1 | * | 8/2005 | Field | 362/523 |

FOREIGN PATENT DOCUMENTS

WO     WO 03023379 A1 * 3/2003

* cited by examiner

LED FLUOROMETER WITH REMOTE DETECTION CAPABILITY

FIELD OF THE INVENTION

The present invention relates to fluorometers. The invention relates particularly to fluorometers for use underwater, especially in the inspection of pipelines, risers, other structures or devices.

BACKGROUND TO THE INVENTION

A fluorometer is an instrument for detecting and, usually, measuring fluorescence. Some substances, for example hydrocarbon substances such as oil, exhibit a natural fluorescence. Other substances may be provided with a fluorescent agent, or tracer, such as fluorescein. A typical fluorometer includes an excitation source, for causing fluorescence in a target substance, and a detector for measuring the resultant fluorescence.

It is known to employ fluorometers in the detection of leaks of fluorescent materials from underwater objects such as pipelines or risers. For example, U.S. Pat. No. 4,178,512 (Frungel) describes a fluorometer for measurements in deep water. The Frungel device comprises a flash lamp unit with detector system orientated at right angles to the lamp. However, the Frungel device is only capable of detecting fluorescent material within a few inches of the lamp/detector. To compensate for the very short range, or point nature, of the measurement, such devices can be used in vertical profiling or simply towed through the water at a varying depths. As a result, such devices may miss significant patches of the fluorescent target thereby giving a false picture of the distribution of the fluorescent species. Such devices are therefore considered to be very inefficient.

GB 2 089 501 (Conoco) discloses an apparatus for detecting hydrocarbons in a body of water, wherein the excitation source comprises a laser which scans the body of water to excite and detect fluorescent materials. The Conoco apparatus is reported as being particularly suited to detecting hydrocarbons on or near the sea surface from a range of several meters. However, because the apparatus is laser-based, it is bulky, expensive and requires a relatively large amount of power. Consequently, such apparatus have restricted use on ROVs (Remotely Operated Vehicles) and particularly AUVs (Autonomous Underwater Vehicles). Moreover, such apparatus suffer from the practicalities associated with health and safety issues surrounding lasers.

U.S. Pat. No. 6,255,118 (Alfano) discloses a fluorometer which employs an LED (Light Emitting Diode) excitation source. However, the LED excitation source is only suitable for exciting material held in a local sample cell. Such devices are not suitable for long range, or remote, detection, particularly underwater.

It would be desirable, therefore, to provide a fluorometer which is capable of remotely detecting fluorescent material, especially in an underwater environment, and which does not suffer from the problems outlined above.

SUMMARY OF THE INVENTION

Accordingly, a first aspect of the invention provides a fluorometer comprising an excitation system including an excitation source for producing excitation light capable of causing fluorescence in fluorescent material; and a detection system for detecting said fluorescence, wherein said excitation source comprises one or more light emitting diodes (LEDs) associated with means for causing said excitation light to form a beam that projects, during use, from the fluorometer. The arrangement is such that the fluorometer is able to detect, fluorescent material located remotely from the fluorometer.

Preferably, said beam causing means comprises a system of at least one lens.

Typically, the arrangement is such that the excitation beam is capable of causing fluorescence in fluorescent material at distances of up to several meters, for example 1 to 15 meters, from the fluorometer.

In some embodiments, the excitation source comprises a single LED. In such embodiments, the excitation beam may comprise a generally circular transverse cross-sectional shape. In alternative embodiments, the excitation source comprises two or more LEDs, preferably arranged in a substantially collinear fashion. In such embodiments, the excitation beam may comprise a generally elliptical transverse cross-sectional shape.

Preferably, the lens system comprises one or more collimating lens.

Advantageously, the beam of excitation light is modulated with a modulating signal having a modulation frequency. Conveniently, the excitation beam is amplitude modulated by said modulation signal.

In preferred embodiments, the detection system comprises a photodetector arranged to received light gathered by said detection system to convert said gathered light into a corresponding electrical signal. Advantageously, an optical filter is associated with said photodetector, the filter being selected to only allow light which is at or around the frequency band of the fluorescent light emitted by a target fluorescent material to reach said photodetector. The preferred detection system further includes, or is associated with, means for performing spectral analysis of the electrical signal produced by the photodetector and means for determining the value of the spectral component of said electrical signal corresponding to said modulation frequency. The value of said spectral component is indicative of the level of detected target fluorescence. Advantageously, the analysis of the electrical signal is performed by a digital signal processor which is preferably included in the detection system.

In some embodiments, the excitation system and the detection system are provided in a respective housing, the respective housings being located adjacent one another and arranged such that there is an overlap, during use, between the excitation beam emanating from the excitation system housing and the field of vision, or detection volume, of the detection system housing. Preferably, the respective housings are adjustably interconnected so that the relative angular disposition of the respective housings may be altered.

In alternative embodiments, the excitation system and the detection system are located in a common housing. In such embodiments, at least some of the excitation system and the detection system are provided in a respective, or a common, inner chamber located internally of the common housing. The excitation system is preferably arranged so that the excitation beam may be projected directly out of the common housing and a collection mirror is provided to direct incoming light to the detection system. In one embodiment, a Cassegrainian mirror system is provided for directing incoming light to the detection system, the Cassegrainian mirror system being located between a first inner chamber containing the excitation system and a second inner chamber containing at least part of the detection system.

Fluorometers embodying the invention are particularly suited for underwater use (or in other liquid or fluid environments), for example on ROVs or other underwater vehicles, or when moored, towed or carried by hand underwater. Other advantageous aspects of the invention therefore include the use of the fluorometer for detecting, tracing and/or tracking fluorescent material, especially quantities or plumes of fluorescent material, in aqueous environments, for example sub sea environments. The invention relates particularly to the detection of fluorescent material that is located remotely of the fluorometer. The fluorometer may advantageously be used to detect leaks from underwater structures, or to detect fluorescent markers or tags on underwater structures.

It is preferred to include a laser pointer system, either internally or externally of the fluorometer, the arrangement being such that the laser beam is substantially aligned with the excitation beam during use.

A second aspect of the invention provides a fluorometer in which the excitation system and the detection system are provided in a respective housing, the respective housings being located adjacent one another and arranged such that there is an overlap, during use, between the excitation beam emanating from the excitation system housing and the field of vision, or detection volume, of the detection system housing.

A third aspect of the invention provides a fluorometer in which the excitation system and the detection system are located in a common housing.

A fourth aspect of the invention provides a method of detecting fluorescent material the method comprising producing a beam of excitation light capable of causing fluorescence in remote fluorescent material; and detecting said fluorescence, wherein said excitation source comprises one or more light emitting diodes (LEDs) associated with a system of one or more lenses, or other beam causing means, in order to produce said beam of excitation light.

Further advantageous aspects of the invention will become apparent to those skilled in the art upon review of the following description of specific embodiments of the invention and with reference to the accompanying drawings.

BRIEF DESCRIPTION OF THE DRAWINGS

Embodiments of the invention are now described by way of example and with reference to the accompanying drawings in which like numerals are used to indicate like parts and in which.

DETAILED DESCRIPTION OF THE DRAWINGS

Figure 1:
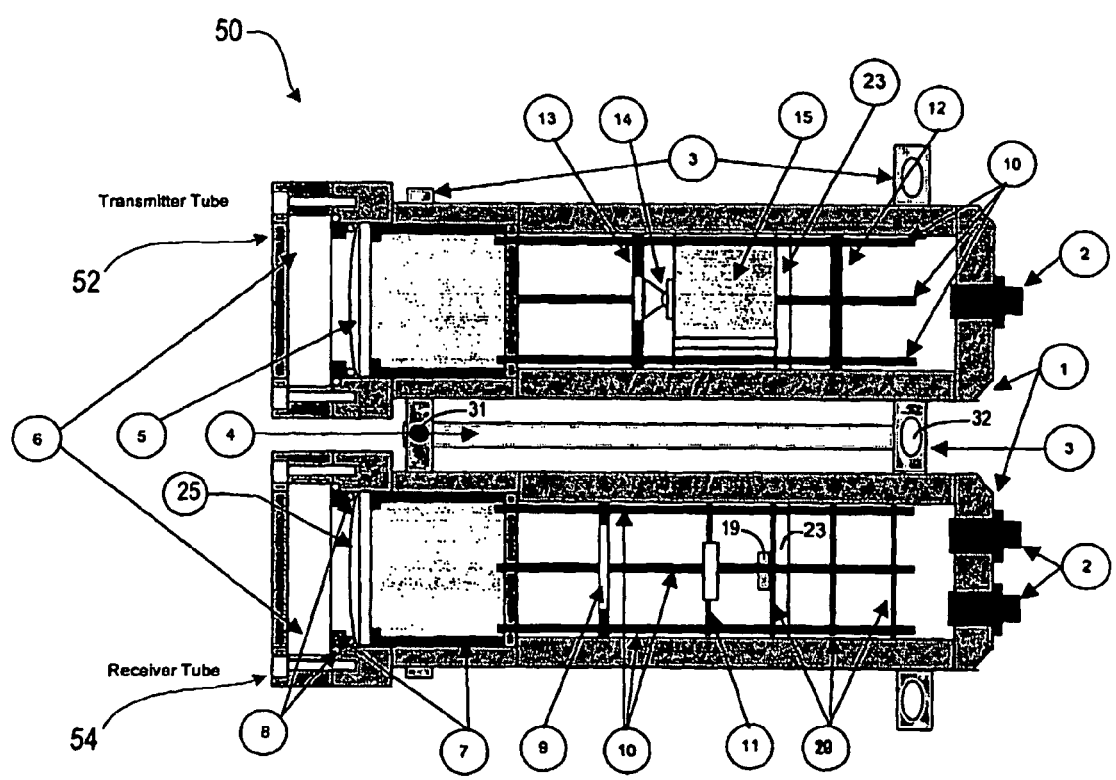
FIG. 1 presents a schematic view of a first embodiment of a fluorometer according the invention.

Referring now to FIG. 1 of the drawings, there is shown, generally indicated as 50, a first embodiment of a fluorometer according to the invention. The fluorometer 50 comprises an excitation unit 52 and a detection unit 54 which, in the present embodiment, are provided as separate, self-contained units. Each unit 52, 54 comprises a respective housing 1 which, by way of example, may be generally tube-like in shape. In the preferred embodiment, the fluorometer 50 is intended for underwater use, and in particular subsea use, and so the housings 1 are configured to be suitably water-tight (see for example water seals 8) and pressure resistant and are preferably formed from a suitable corrosion-resistant material.

The units 52, 54 are mechanically interconnectable by means of a frame 3 or other mechanical linkage, preferably in a side-by-side arrangement as illustrated in FIG. 1, or an over and under arrangement. The preferred arrangement is such that the relative angular disposition between the units 52, 54 is adjustable. In FIG. 1, the units 52, 54 are shown in a first operational mode in which their respective longitudinal axes are substantially parallel with one another. In alternative modes of operation (not illustrated) the units 52, 54 are disposed such that their respective longitudinal axes are convergent in a direction generally forward of the fluorometer (i.e. in a direction generally towards the target material, or in the general direction in which an excitation beam emanates from the unit 52). In the embodiment of FIG. 1, the frame 3 includes a pivotable link 31 and a detachable link 32 located rearwardly of the pivotable link 31. When the detachable link 32 is in a detached state, the relative angular disposition of the units 52, 54 is adjustable via the pivotable link 31. The link 31 may be extendible rather than, or as well as, being detachable. In alternative embodiments (not illustrated), the units 52, 54 may be mechanically interconnectable by any other suitable means, preferably such that the units 52, 54 are pivotable or movable with respect to one another about an axis that is generally perpendicular to a plane common to both units 52, 54. The adjustable interconnection between the units 52, 54 may be automated for remote activation during use.

Each unit 52, 54 conveniently includes respective internal support bars 10 on which the various components of the unit 59, 54 may be mounted as described hereinafter.

The excitation unit 52 comprises an excitation source 14 comprising one or more light emitting diodes (LEDs). Typically, LEDs emitting electromagnetic radiation, i.e. light, in the range 430 nm to 500 nm are suitable for use in the excitation source 14, although it will be understood that other emission wavelengths may be used as suits the application. By way of example, high flux LEDs are suitable. Suitable LEDs may for example have a typical luminous flux (lm) in the range 18 to 30. Advantageously, the excitation source 14 is associated with a heat sink 15.

Preferably, an optical filter 13 is provided to filter the light emitted by the excitation source 14, the preferred arrangement being such that it optimises the coincidence with the absorption of the target fluorescent material. For example, for applications in which it is desired to detect fluorescein, the optical filter 13 is preferably selected to pass light within the range 450 nm to 470 nm. In the preferred embodiment, the optical filter is located adjacent the excitation source 14. Alternatively, the optical filter 13 may be located at any position between the excitation source 14 and the window 6 (including on either side of the lens system 5) provided it is arranged to filter substantially all of the light emitted by the excitation source 14.

It is also preferred to provided a collimator, e.g. a collimating lens, hood or reflector, adjacent the excitation source 14 in order to collimate the light emitted therefrom. The collimator reduces the divergence of the emitted light (preferably to produce a substantially parallel beam). This reduces light scatter within the housing 1 and so reduces optical noise. The collimator may be integrally formed with the excitation source 14 (as shown in FIG. 1 where the LED 14 includes a housing or cover which provides a collimating effect on the light emanating therefrom).

A lens system 5 is provided to control the divergence of the light emitted from the unit 52. Preferably, the lens system 5 comprises a collimating lens system arranged to receive light emanating from the excitation source 14 and to produce a beam of light (not shown in FIG. 1) which is generally circular or generally elliptical in transverse cross-section. In the preferred embodiment, the lens system 5 comprises a single collimating lens. The collimating lens 5 is normally positioned within the housing such that the LED light incident on the lens 5 emanates substantially from the focal point of the lens 5. In some embodiments, this may be achieved by locating the excitation source 14 substantially at the focal point of the lens 5. It will be understood, however, that the relative position of the lens 5 and excitation source 14 may be affected by intermediate components, e.g. the collimator adjacent the excitation source 14. In alternative embodiments, the lens system 5 may comprise more than one lens and the relative position of the lens 5 and excitation source 14 may be adjusted accordingly. In the preferred embodiment, the position of the collimating lens 5 may adjustable in a direction substantially parallel with the longitudinal axis of the housing 1 (and therefore the longitudinal axis of the beam produced by the excitation source 14) by means of any suitable mechanism, e.g. a helical screw mechanism (not shown). The collimator and the lens system 5 provide means for causing the excitation source to form a beam. In alternative embodiments, other conventional beam causing means may be used.

The transverse cross-sectional shape of the beam emanating from the excitation unit 52 during use may be adjusted by any suitable means. For example, a single LED excitation source 14 in conjunction with a collimating lens system 15 normally produces a beam of substantially circular cross-section. However, by providing the excitation source 14 with more than one LED arranged in a line or in a collinear manner (one dimensional array), or arranged in a generally rectangular elongate two dimensional array, a beam of generally elliptical transverse cross-section may be produced. Alternatively, or in addition, one or more lenses (not shown), e.g. a cylindrical or astigmatic lens, may be provided between the excitation source 14 and the window 6—this too can create a beam of generally elliptical transverse cross-section. Alternatively still, or in addition, the shape of the LED housing or cover may be selected to shape the beam such that it has a generally elliptical transverse cross-section.

Electronic control circuitry 12 is provided for controlling the supply of electrical current to and for stabilising the optical power of; the excitation source 14 (e.g. for applying amplitude modulation as is described in more detail below). The excitation source 14 may also communicate with or be controlled by a system processor (not shown in FIG. 1), conveniently via circuitry 12. In the present embodiment, the system processor is provided in the detection unit 54 as is described in further detail below. In addition, the unit 52 is conveniently provided with a conventional external connector 2 for supplying electrical power and allowing data transmission (e.g. via as RS-232 interface) to and from an external system (not shown).

In the preferred embodiment, the fluorometer includes, or is associated with means for modulating the excitation beam, preferable by amplitude modulation. The modulation means is conveniently provided in the control circuitry 12. Conveniently, the light emitted by the excitation source 14 is modulated, conveniently by amplitude modulation. This may conveniently be achieved by controlling the current supplied to the excitation source 14 in accordance with a desired modulation signal. By way of example, the light may be amplitude modulated at a frequency of approximately 750 Hz although it will be understood that other modulation frequencies may be used as suits the application.

The light beam produced by the lens system 5 passes through an optical plate or window 6 into the surrounding environment. The window 6 may be optically passive (e.g. plain glass or plastics) or may be active (i.e. comprise a lens) to assist in the shaping of the beam.

Figure 2:
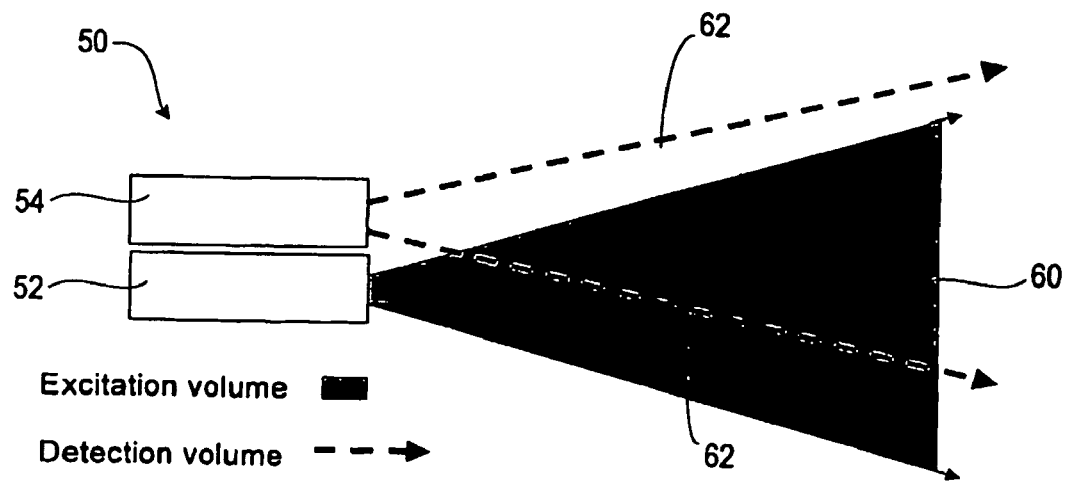
FIG. 2 presents a stylised plan view of the fluorometer of FIG. 1 during use.
Figure 3:
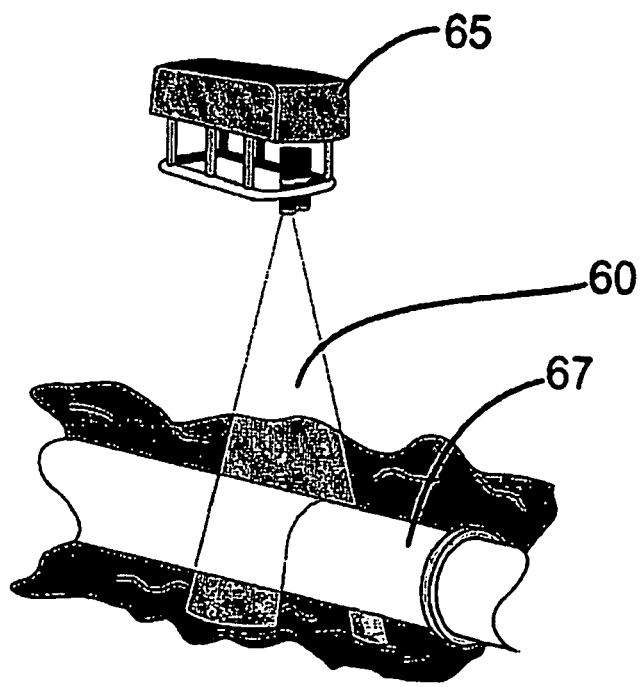
FIG. 3 shows the fluorometer in use mounted on an ROV inspecting an underwater pipeline.

FIG. 2 illustrates the light beam 60 produced by the excitation unit 52. It will be seen that the excitation beam 60 is divergent in a direction generally forward of, or away from, the unit 52. The beam 60 is generally conical in shape, having a generally circular or elliptical transverse cross-section, and so defines a generally conical excitation volume. i.e. a target volume in which fluorescent material is excited by the excitation beam 60. When used underwater, the excitation volume comprises a body of water. This is illustrated in FIG. 3 which shows an underwater vehicle 65, such as an ROV or AUV, carrying the fluorometer 50. The excitation beam 60 is incident on and around an underwater pipeline 67. The pipeline 67 carries a load, typically of liquid or gaseous form, which exhibits fluorescence (either inherently or as a result of an added fluorescent tracer). Should there be a leak in the pipeline 67, then fluorescent material will be present at or around the pipeline 67 in the vicinity of the leak. When such fluorescent material falls within the excitation beam 60 it is caused to fluoresce thereby emitting light in a frequency band which depends on the characteristics of the fluorescent material or species. In this example as the ROV 65 navigates along the pipeline 67, the light beam 60 is directed onto the pipeline 67 at an altitude or distance of typically a few meters, the pipeline 67 may thus be efficiently monitored for leaks.

It will be seen from the foregoing that the fluorometer 50 is capable of causing excitation of fluorescent material remotely, i.e. up to several meters from the fluorometer 50. This is because the light emanating from the excitation source 14 is manipulated to form an excitation beam 60, as described above. For typical underwater applications, for example for the inspection of pipelines risers and similar structures, the excitation unit 52 is arranged to produce a beam 60 that is able to encompass a typical riser, pipeline or other structure and the surrounding water. By way of example, the beam 60 may be approximately 1 meter wide at a distance of approximately 1.5 meters from the window 6 of the unit 52, although these dimensions may change depending on the application.

The detection unit 54 includes a fluorescence detection system for detection of fluorescence emanating from a substantial part of the excitation volume illuminated by the excitation beam 60. The intensity of this fluorescence is indicative of the concentration of the target fluorescent material in the illuminated excitation volume. The detection unit 34 includes an optical plate or window 6, which may be similar to the window 6 of the excitation unit 52, and a lens system 25. The lens system 25 of the detection unit 54 is arranged to define a detection volume from which light is directed or focussed onto a photodetector 19. The detection volume is illustrated in FIG. 2 defined by broken lines 62. Typically, the detection volume 62 is generally conical in shape. Because the excitation unit 52 and the detection unit 54 are located adjacent one another, there is an overlap volume defined by the overlap of the excitation volume 60 and the detection volume 62. The detection unit 54 is able to detect fluorescence caused by the excitation beam 60 which is present in the overlap volume.

The lens system 25 may comprise one or more lenses. The lens system 25 may include a collimating lens for shaping the received light so that it may better be directed onto the photodetector 19. The lens system 25 may alternatively, or in addition, include a field lens which, when the collimating lens is present, is located beyond the collimating lens with respect to the photodetector 19.

It is preferred that the detectable fluorescent light is filtered before reaching the photodetector 19. Hence, the detection unit 54 may include an optical filter 11 between the photodetector 19 and the lens system 25. The optical filter 11 is selected light to allow only light within the emission range of the target fluorescent species to reach the photodetector 19.

It is also preferred to provide a light baffle 9 in the path of the received fluorescent light, preferably between the lens system 25 and the filter 1, in order to reduce the amount of scattered light received by the photodetector 19.

The photodetector 19 may comprise any suitable conventional device for converting optical signals into electrical signals, for example a conventional photodiode or photomultiplier. The photodetector 19 receives a focussed or substantially focussed, and preferably optically filtered, optical signal comprising the received fluorescent light and produces a corresponding electrical signal. The characteristics of the electrical signal are indicative of the concentration of the target fluorescent material in the illuminated excitation volume.

Figure 4:
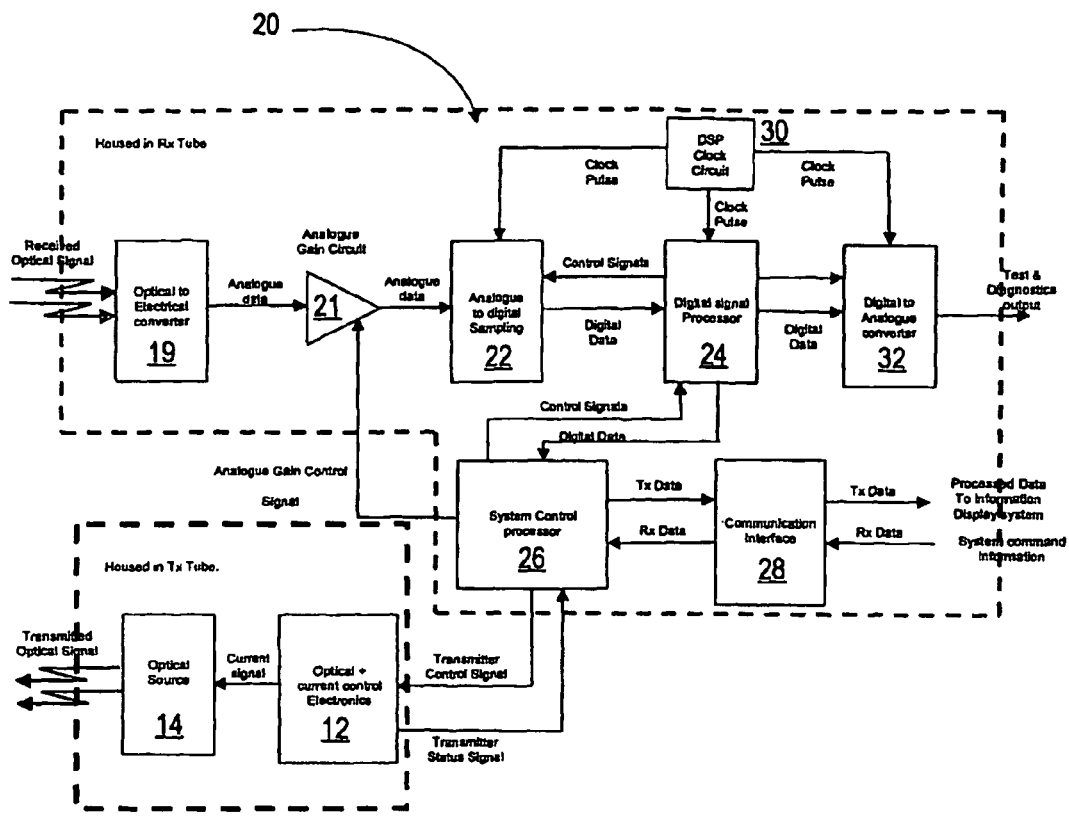
FIG. 4 presents a block diagram of a signal processing system suitable for use in the fluorometer of FIG. 1.

The detection unit 54 includes a processing system 20 for receiving and analysing the electrical signal produced by the photodetector 19. A preferred embodiment of the processing system 20 is illustrated in FIG. 4. The received electrical signal, which is analogue in form, is provided to an analogue-to-digital converter (ADC) or sampling device 22, preferably via a gain controllable amplifier 21. The ADC 22 produces a digital signal which is representative of the received electrical signal. The digital signal is provided to a digital signal processor 24 for analysis. In this connection, the fluorescent light caused by the excitation beam 60 is modulated in a manner similar to the modulation of the excitation beam 60. Hence, the electrical signal produced by the photodetector 19 comprises a signal component corresponding to, or caused by, the modulation of the excitation beam 60. The amplitude of this modulation signal component is indicative of the intensity of the fluorescent light caused by the interaction of the excitation beam 60 and the target fluorescent material. In the preferred embodiment, the digital signal processor 24 provides means for detecting the modulation component. The digital signal processor 24 is arranged to measure, or obtain, the amplitude, or value, of the signal component of the received digital signal which is present at, or substantially at, the modulation frequency of the excitation beam 60. Advantageously, the digital signal processor 24 is arranged to detect a signal component having substantially the same phase as the excitation beam 60. In the preferred embodiment, therefore, the digital signal processor 24 is arranged to measure, or obtain, the amplitude, or value, of the signal component of the received digital signal which is present at, or substantially at, the modulation frequency of, and in substantially the same phase as, the excitation beam 60, or the phase of the modulation component of the excitation beam 60. To this end, the circuitry 20 and in particular the digital signal processor 24 is required to know the phase characteristics of the excitation beam 60, or more particularly the phase of the modulation component of the excitation beam 60. In the preferred embodiment, this is readily achieved since the control circuitry 12 in the excitation unit 54 is controlled by the circuitry 20, in particular the system processor 26. Hence, circuitry 12 applies the modulation characteristics to the excitation beam 60 under the control of the processor 26 and so the characteristics of the modulation, including phase, is known to the processor 26: The processor 26 may supply this information to the digital signal processor 24 for comparison with the received signal.

By way of example, the digital signal processor 24 may transform the received digital signal into the frequency domain, e.g. using the Fast Fourier Transform (FFT), and measure, or obtain, the amplitude, or value, of the resulting spectral component in a frequency band at or around the modulation frequency. Modulating the excitation beam 60 and detecting fluorescent signals at the modulation frequency, reduces the possibility that the detection unit 54 may make a false or inaccurate detection as a result of interference from, for example, background noise in the relevant frequency band.

By way of example, where the excitation beam 60 is modulated, the digital signal processor 24 determines the level of detected fluorescence from the target fluorescent material by measuring, or obtaining, the amplitude, or value, of the spectral component of the in phase component of the detected signal at the modulation frequency. The ADC 22 should sample the electrical signal at least twice the modulation frequency.

The processing system 20 preferably also includes a system control processor 26 for receiving and analysing data provided to it by the digital signal processor 24. The digital signal processor 24 provides to the system processor 26 data comprising the detected value of the return or received signal. The processing system 20 preferably includes a communication interface 28 by which the system processor 26 may communicate with a remote system (not shown), for example an information display system (to this end the detection unit 54 includes one or more connectors 2 for allowing data transmission to and from the unit 54 and, in some embodiments, also for supplying power to the unit 54). The system processor 26 may communicate data relating to the detected intensity of target fluorescent material to external systems via the interface 28. In the preferred embodiment, the system processor 28 includes an analysis routine for comparing the measured value of the spectral component at the modulation frequency (i.e. the detected intensity of target fluorescent material) against one or more threshold levels and, if one or more thresholds are exceeded, for generating one or more alarm signals. The alarm signals may be sent to an external system via the interface 28. Preferably, the system processor 26 causes an audible alarm to be generated, either locally or remotely, if detected fluorescence levels exceed a pre-determined threshold. This is particularly useful in applications where the fluorometer is carried by an ROV, or the like, since the ROV operator may ignore the fluorometer until an audible alarm is heard.

The digital signal processor 24 and the ADC 22 are conveniently provided with a common clock signal from an on board oscillator 30. A digital-to-analogue converter 32 may also be provided to allow the digital signal processor 24 to provide outputs for testing and diagnostic purposes.

The detection unit 54 allows target fluorescent material, and in particular relatively high concentrations thereof, to be detected in real time, thereby giving an immediate indication of likely leak locations. This allows a concentration map of detected target fluorescence to be generated.

In FIGS. 1 and 2, the fluorometer 50 is shown in a first mode of operation wherein the respective longitudinal axes of the excitation and detection units 52, 54 are substantially parallel with one another and the excitation beam 60 and the detection volume 60 are substantially aligned with, or centred on, the respective longitudinal axis. In this mode of operation, the shape of the overlapping volume defined by the overlap of the excitation volume 60 and the detection volume 62 enables the fluorometer 50 to detect fluorescence remotely from a distance of several meters. However, in some applications there may be complex plume patterns of the target fluorescent species present due to multiple leaks or a high background level of target fluorescent material. In such cases the fluorescence from this material can make it difficult to remotely locate the source of a leak. In order to suppress the contribution of such background fluorescence it is desirable to be able to preferentially select the region of the water containing the object being inspected for leaks, e.g. a pipe. In the embodiment of FIG. 1, this is achieved by varying the region of overlap of the excitation beam 60 (or excitation volume) and the detection volume 62. In the preferred embodiment, this is may be performed by adjusting the relative angular disposition of the two units 52, 54 with respect to one other so that the respective longitudinal axes converge in a direction generally forward of the fluorometer 50. This has the effect of adjusting or limiting the overlap of the excitation beam 60 and the detection volume 62 to a finite region relatively close, e.g. 2 to 4 meters, to the fluorometer 50. Alternatively, or in addition, the divergence of the excitation beam 60 may be altered. This may be achieved by, for example, adjusting the distance between the excitation source and the lens system 5 and/or selection of a lens system 5 with appropriate characteristics and/or by adjusting the spacing between LEDs at the excitation source. Alternatively still, the angle of the beam 60 and/or detection region 62 with respect to the respective longitudinal axis may be altered. This arrangement allows the suppression of background fluorescent material remote from the region of interest and thus improves the leak detection process.

Figure 5:
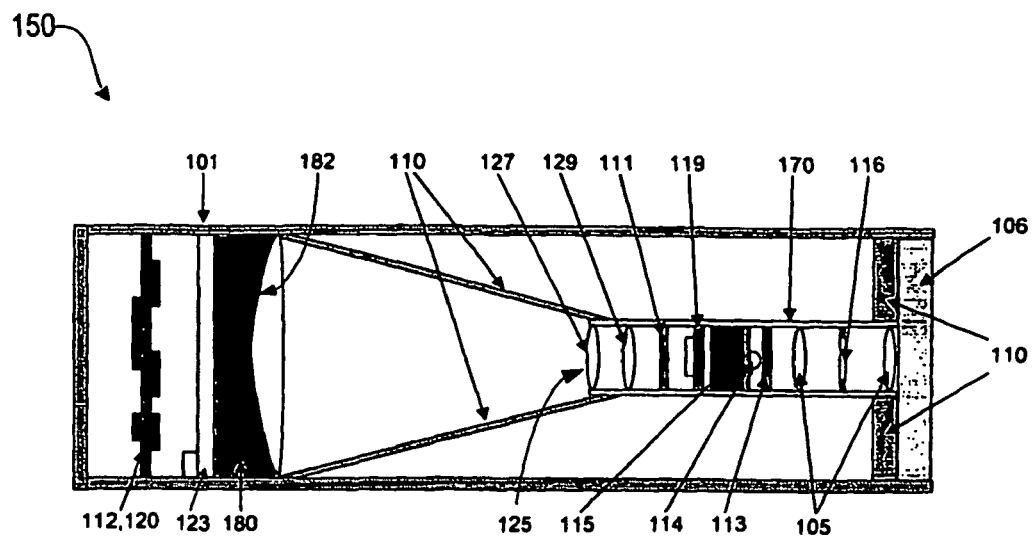
FIG. 5 presents a schematic view of a second embodiment of a fluorometer according the invention.
Figure 6:
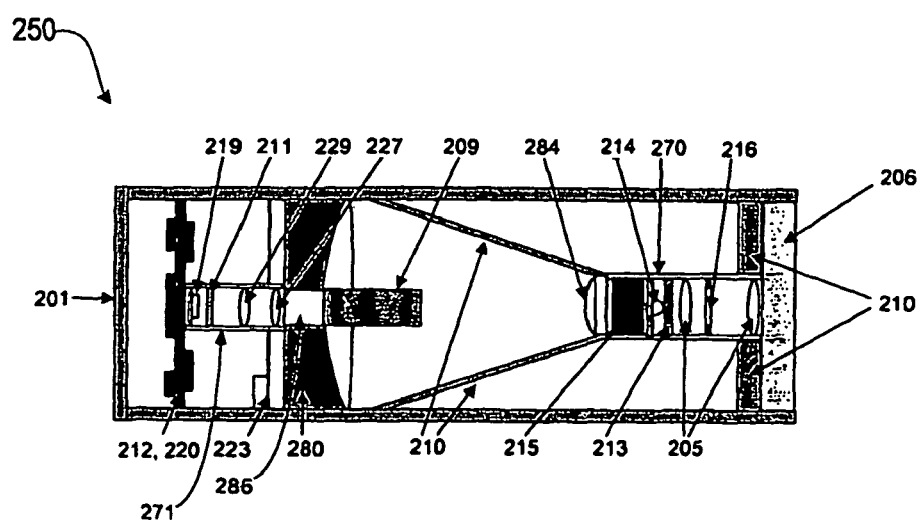
FIG. 6 presents a schematic view of a third embodiment of a fluorometer according the invention.

FIGS. 5 and 6 illustrate respective alternative embodiments of a fluorometer according to the invention in which the excitation system and the detection system are included in a single unit or housing.

Referring to FIG. 5, a fluorometer 150 is shown comprising a main housing 101 which, by way of example, may be generally tube-like in shape. In the preferred embodiment, the fluorometer 150 is intended for underwater use, and in particular subsea use, and so the housing 101 is configured to be suitably water-tight and pressure resistant and is preferably formed from a suitable corrosion-resistant material. The housing 111 includes an optical window or plate 106 (which may be optically active or passive) through which light may be projected and received.

An inner housing or chamber 170 is provided internally of the main housing 101 and is preferably located substantially on or along the longitudinal axis of the main housing 101. The inner chamber 170 is generally tube-like or sleeve-like and is formed from a material that is substantially impermeable to light. Mechanical supports 110 are provided for holding the inner chamber 170 in its desired location. The inner chamber 170 contains the excitation system including an excitation source 114, heat sink 115 and, preferably, optical filter 113 which may be generally similar to the corresponding components of the embodiment of FIG. 1 and to which similar descriptions apply. The excitation system also includes a lens system 105, and in particular a collimating lens system, for controlling, and in particular reducing, the divergence of the light beam produced by the excitation source 114. In FIG. 5, the lens system 105 is shown to comprise two spaced apart collimating lenses, although in alternative embodiments, a single collimating lens, or more than two, may be provided. An aperture stop 116 may advantageously be associated with the lens system 115 (e.g. located between the two lenses of system 105) for restricting the occurrence of stray light. The excitation system produces an excitation beam (not shown) which is generally similar to the beam 60 produced by the fluorometer 50 and which is projected from the fluorometer 150 via window 106. Electronic control circuitry 112 is provided for controlling the excitation system, including the modulation of the excitation beam, and may be generally similar to the circuitry 12 of FIG. 1.

The inner chamber 170 also houses at least some of the components of the detection system including a photodetector 119, preferably an optical filter 111 and a lens system 125 each of which may be generally similar to the corresponding components of the fluorometer 150 and to which similar descriptions apply. The lens system 125 is located at or adjacent an open end of the chamber 170, which open end is opposite the open end at which the lens system 105 of the excitation system is located (i.e. opposite from where the excitation beam emanates). The lens system 125 is arranged to receive light and to focus or direct the received light onto the photodetector 119, preferably via optical filter 111. The lens system 125 may comprise a field lens 127 and a collimating lens 129 or may alternatively comprise only a collimating lens. When present, the field lens 127 is located at or adjacent the open end of the chamber 170 and is arranged to extend the field of view of the detection system housed within the chamber 170 and to direct light onto the collimating lens 129. The collimating lens 129 further reduces the divergence of the received light, advantageously producing a generally parallel beam of light directed onto, or focussed onto, the photodetector 119. In one embodiment, the heat sink 115 may divide the chamber 170 into first and second portions, one portion containing the excitation components, the other containing detection components. To this end, the heat sink 115 may substantially fill the chamber 170 so that light is substantially prevented from passing between the chamber portions. Alternatively, the chamber 170 may be similarly divided by any other suitable means.

The detection system further includes a collection mirror 180 located inside the main housing 101 but outside of the inner housing 170. In the preferred embodiment, the detection system, including mirror 180, and the excitation system are substantially collinear, i.e. the excitation source 114, the lens systems 125, 105, the photodetector 119 and the mirror 180 are centred substantially on or around a common axis, conveniently the longitudinal axis of the housing 101. Hence, the respective focal points of the mirror and lenses lie substantially on a common axis.

The collection mirror has a light reflecting surface 182 which is generally concave (and may for example be substantially parabolic) and which faces the optical window 106. The arrangement is such that fluorescent light, entering the housing 101 via the area of window 106 which surrounds the inner chamber 170, is incident upon the reflective surface 182 of the mirror 180 and is reflected towards the open end of the inner chamber 170 which carries the lens system 125. The preferred arrangement is such that the lens system 125, or more particularly the field lens 127 is located substantially at the focal point of the mirror 180. Hence, light gathered by the mirror 180 is focussed onto the field lens 127.

A processing system 120 is provided for receiving and analysing the electrical signal produced by the photodetector 119. The processing system 120 may be generally similar to the processing system 20 illustrated in, and described with reference to, FIG. 4.

Referring now to FIG. 6, there is shown a third embodiment of a fluorometer 250 embodying the invention. The fluorometer 250 is generally similar to the fluorometer 150 and like numerals are used to indicate like parts. The housing 201 includes a first inner chamber 270 which is generally similar to the inner chamber 170 of fluorometer 170 and contains the excitation system including excitation source 214, heat sink 215, optical filter 213 and lens system 205, all of which may be similar to the corresponding components of fluorometer 150 and to which corresponding descriptions apply. A primary mirror 280 is provided in the housing 201 and may be arranged within the housing in a manner similar to mirror 180 of fluorometer 150 in order to collect light which enters the housing 201 via window 206. A secondary mirror 284 is provided substantially at the focal point of the primary mirror 280. The secondary mirror 284 is arranged to reflect the light focused, or directed, onto it by the primary mirror 280 such that the reflected light is brought to a focus substantially at an aperture 286 formed in the primary mirror 280, preferably at the centre of the primary mirror 280. In the preferred embodiment, the primary mirror 280 and secondary mirror 284 together comprise a Cassegrainian mirror system wherein the reflecting surface of the primary mirror 280 is generally paraboloidal in shape and the reflecting surface of the secondary mirror 284 is Generally hyperboloidal in shape. Preferably, a light baffle 209 is provided at or adjacent the aperture 286 to guide the reflected light through the aperture 286. The detection system is located beyond the primary mirror 280 (with respect to the window 6) in a second inner housing 271. The second inner housing or chamber 271 contains the lens system 225 (preferably including field lens 227 and collimating lens 229), optical filter 211 and photodetector 219, each of which may be generally similar in form and arrangement to the corresponding components in the inner chamber 170 of fluorometer 150 and to which similar descriptions apply. The reflected light which passes through the aperture 286 is received by the lens system 225 and processed by the detection system in a manner substantially similar to that described for fluorometers 50, 150. In the preferred embodiment, the detection system, including mirrors 280, 284, aperture 286 and the excitation system (or at least the respective longitudinal axis of the systems), are substantially collinear, as for the arrangement of FIG. 5.

A processing system 220 is provided for receiving and analysing the electrical signal produced by the photodetector 219. The processing system 220 may be generally similar to the processing system 20 illustrated in, and described with reference to, FIG. 4.

The provision of the primary and secondary mirrors 280, 284 folds or bends the path of the received light through the housing 201 with the result that the overall length of the housing 201 may be reduced.

Figure 7:
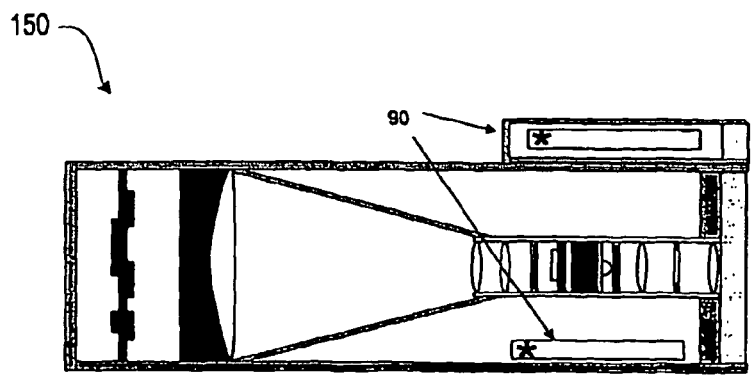
FIG. 7 presents a schematic diagram of an embodiment of a fluorometer including a laser targeting system.

During use, it can be important to ensure that the fluorometer 50, 150, 250 is monitoring the target underwater object e.g. pipeline or riser. When underwater currents are present, the fluorometer 50, 150, 250 may not be pointed directly at the target in order to compensate for the effects of the current on the excitation beam and fluorescent light. It is therefore preferred to incorporate a laser pointer system 90 (see FIG. 7) either into or onto the housing 1, 101, 201 such that a laser beam (not shown) may be provided which projects, during use, generally forwardly of the fluorometer 50, 150, 250 and generally parallel with, or collinear with, the centre of the excitation beam, which in the preferred embodiments is generally along or parallel with the longitudinal axis of the housing 1, 101, 201. The laser pointer 90 comprises a laser source (not shown) for producing a laser beam at a wavelength that is both clearly visible to the operator and distinct from the wavelength of the excitation beam. Typically, the pointer 90 may be a double diode pumped Nd:YAG system operating at 532 nm or a laser diode system operating at 665 nm. The laser pointer beam may provide a dot or a distinct pattern such as a cross on its target. As ROVs and mini-sub type vehicles are routinely navigated under water by an operator using cameras mounted on the vehicle, the laser pointer 90 will allow the operator of an ROV or mini-sub to easily see if the target is being effectively monitored for leaks. To further improve the efficiency and ease of use of the fluorometer 50, 150, 250, it may be mounted on the same pan-and-tilt stage (not shown) as the operator's camera or may be carried by a separate but synchronised pan-and-tilt stage (not shown). In this way as long as the operator keeps the camera pointed and centred on the target the excitation beam is also pointed at the target.

In some underwater monitoring applications it may be that there are multiple objects, for example pipes, in close proximity to one another. To facilitate the monitoring of discrete objects, or sections of objects, in such cases the system may include a zooming system on both the excitation and/or detection units. This allows the divergence of excitation beam and the effective collection angle of the detection system to be varied such that the fluorometer 50, 150, 250 is targeting a smaller volume, thus making it easier to monitor closely packed objects. For the excitation system, the zooming system may be implemented by slidably mounting one or both of the excitation source 14, 114, 214 and the lens system 5, 105, 205 within the housing 1, 101, 201. By way of example, in the embodiments of FIGS. 1, 5 and 6, the excitation source 14, 114, 214 is slidably mounted, by any convenient means, in the housing 1, 101, 201 for sliding movement in a direction towards or away from the lens system 5, 105, 205. Movement of the excitation source 14, 114, 214 may be achieved by any suitable means, for example a helical screw mechanism 23. For the detection system, the zooming system may be implemented by slidably mounting one or both of the photodetector 19, 119, 219 and the lens system 25, 125, 225, or the mirror 180, 280 within the housing 1, 101, 201. By way of example, in the embodiment of FIG. 1, the photodetector 19, 119, 219 is slidably mounted, by any convenient means, in the housing 1 for sliding movement in a direction towards or away from the lens system 25, 125, 225. In the embodiments of FIGS. 5 and 6, the mirror 180, 280 is slidably mounted, by any convenient means, in the housing 101, 201 for sliding movement in a direction towards or away from the lens system 25, 125, 225 or secondary mirror 284. Movement of the photodetector 19, 119, 219 or mirror 180, 280 may be achieved by any suitable means, for example a helical screw mechanism 23, 123, 223.

It will be understood that the selection of LEDs and optical filters is application dependent. For example, by using one or more LEDs with shorter emission spectrum wavelength, e.g. around 350 nm, and using corresponding optical filters, e.g. with a pass band of around 300-400 nm, the fluorometer 50, 150, 250 may be used to excite and detect fluorescence in oil.

It will be understood from the foregoing that in preferred embodiments of the invention, the excitation source 14, 114, 214 comprises one or more LEDs and is associated with a lens system in order to produce the excitation beam. LEDs are safer than lasers and require less power. Accordingly, the fluorometers 50, 150, 250 may be smaller, lighter and less expensive than alternative laser-based devices. Moreover, by using more than one LED, the transverse cross-sectional shape or size of the excitation beam can be adjusted to suit a desired application without adding significantly to the amount of power required by the excitation source. For example, two or more LEDs may be arranged in a collinear fashion to produce a beam which is generally elliptical in transverse cross-section, the number of LEDs used determining the width or breadth of the beam.

However, it will also be understood that various aspects of the fluorometers described herein may be used with alternative excitation sources, e.g. laser excitation sources, while still benefiting from various advantageous aspects of the invention as described herein.

The invention is not limited to the embodiments described herein which may be modified or varied without departing from the scope of the invention.

The invention claimed is:

1. A fluorometer for detecting the level of fluorescent material in a body of water, the fluorometer comprising:
    an excitation system including an excitation source for producing excitation light capable of causing fluorescence in fluorescent material; and
    a detection system for detecting said fluorescence, wherein
        said excitation system comprises an excitation source comprising one or more light emitting diodes (LEDs), the excitation system further comprising means to cause said excitation light to form, in use, a generally conical divergent beam projecting from the fluorometer, said beam causing means comprising at least one collimating lens, said excitation system further including means for modulating said beam with a modulating signal having a modulating frequency, and wherein
        said detection system comprises means for receiving light and for converting said received light into a corresponding electrical signal, and at least one lens arranged to direct said received light onto said light receiving and converting means, wherein said at least one lens of the detection system is arranged to provide a generally conical convergent detection volume for the detection system, said generally conical detection volume converging in a direction towards said fluorometer and at least partially overlapping with said generally conical divergent beam and wherein
        said detection system further includes means for detecting, in the electrical signal produced by said light receiving and converting means, a signal component of substantially the same frequency as said modulation frequency, said detecting means including means for performing spectral analysis of said electrical signal and means for determining the value of a spectral component of said electrical signal corresponding to said modulation frequency,
        wherein said detection system is arranged to determine the level of fluorescent material present in said body of water depending on said value of said spectral component, such that the fluorometer is capable of detecting fluorescent material located remotely from the fluorometer in said body of water.

2. A fluorometer as claimed in claim 1, wherein said excitation source is located substantially at the focal point of the nearest to the excitation source of said at least one lens.

3. A fluorometer as claimed in claim 1, wherein said excitation system includes a collimator for forming said generally conical divergent beam.

4. A fluorometer as claimed in claim 1, wherein said excitation source comprises a plurality of LEDs arranged in a generally rectangular and at least one dimensional array.

5. A fluorometer as claimed in claim 1, wherein said modulating means is arranged to amplitude modulate said beam.

6. A fluorometer as claimed in claim 5, wherein said modulating means is arranged to modulate said beam by adjusting the power supply of the excitation source in accordance with said modulating signal.

7. A fluorometer as claimed in claim 1, wherein said light receiving and converting means comprises a photodetector.

8. A fluorometer as claimed in claim 1, wherein said light receiving and converting means is located substantially at the focal point of the nearest to said light receiving and converting means of said at least one lens.

9. A fluorometer as claimed in claim 1, wherein said detecting means is arranged to detect, in the electrical signal produced by said light receiving and converting means, a signal component of substantially the same frequency as said modulation frequency and substantially in phase with the modulation of said beam.

10. A fluorometer as claimed in claim 1, wherein the excitation system and the detection system are each provided in a respective housing, the respective housings being located adjacent one another and arranged such that there is an overlap, during use, between said generally conical divergent beam emanating from the excitation system housing and said generally conical convergent detection volume of the detection system housing.

11. A fluorometer as claimed in claim 10, wherein the respective housings are adjustably interconnected so that the relative angular disposition between the respective housings may be altered such that the distance of said overlap from said respective housings is altered.

12. A fluorometer as claimed in claim 11, wherein the respective housings lie generally in a common plane, the relative angular disposition of the housings being alterable about an axis that is substantially perpendicular to said plane.

13. A fluorometer as claimed in claim 1, wherein the excitation system and the detection system are located in a common housing.

14. A fluorometer as claimed in claim 13, wherein said common housing comprises a window and at least one inner chamber, at least part of the excitation system and at least part of the detection system being located in said at least one inner chamber, said at least part of the excitation system being arranged so that said beam is projected, during use, out of the housing through said window, said at least part of the detection system facing away from said window, and wherein a reflecting surface is located inside the housing facing said window and beyond the detection system with respect to said window, said reflecting surface being arranged to direct light entering, during use, said housing through said window onto said detection system.

15. A fluorometer as claimed in claim 14, wherein said at least part of the excitation system and said at least part of the detection system are located substantially co-axially with one another within said housing.

16. A fluorometer as claimed in claim 14, in which said at least one inner chamber is located substantially on the longitudinal axis of said housing.

17. A fluorometer as claimed in claim 13, wherein said common housing comprises a window and at least two inner chambers, at least part of the excitation system being located in a first inner chamber and at least part of the detection system being located in a second inner chamber, said at least part of the excitation system being arranged so that said beam is projected, during use, out of the housing through said window, said second inner chamber being located beyond said first inner chamber with respect to said window, said at least part of the detection system facing towards said window, and wherein a reflecting system is located between the first and second inner chambers and is arranged to direct light entering, during use, said housing through said window onto said detection system.

18. A fluorometer as claimed in claim 17, wherein said reflecting system comprises a first reflecting surface facing towards said window and a second reflecting surface facing away from said window, the first reflecting surface being arranged to direct light entering, during use, said housing through said window onto said second reflecting surface, said second reflecting surface being arranged to direct said light onto said detection system.

19. A fluorometer as claimed in claim 18, wherein said first reflecting surface is shaped to define an aperture, said detection system being positioned to receive light from said second reflecting surface through said aperture.

20. A fluorometer as claimed in claim 17, wherein said reflecting system comprises a Cassegrainian mirror system.

21. A fluorometer as claimed in claim 1, further including a laser device carried by the fluorometer and positioned to project, during use, a laser beam in a direction generally parallel, or aligned, with the excitation beam.

22. A fluorometer as claimed in claim 1, wherein the fluorometer comprises at least one housing, the or each housing comprising a window through which said excitation beam is projected during use and/or through which light is received during use, wherein said excitation source is slidably moveable towards and away from the window of the housing in which it is located.

23. A fluorometer as claimed in claim 1, wherein the fluorometer comprises at least one housing, the or each housing comprising a window through which said excitation beam is projected during use and/or through which light is received during use, wherein at least one lens of said lens system is slidably moveable towards and away from the window of the housing in which it is located.

24. A fluorometer as claimed in claim 14, wherein the fluorometer comprises at least one housing, the or each housing comprising a window through which said excitation beam is projected during use and/or through which light is received during use, wherein at least one reflecting surface is slidably moveable towards and away from the window of the housing in which it is located.

25. A fluorometer as claimed in claim 9, further including means for determining the amplitude of said signal component, and means for generating an alarm when said amplitude exceeds a threshold.

26. A fluorometer as claimed in claim 1, provided on an underwater vehicle.

27. A vehicle as claimed in claim 26, wherein the vehicle includes at least one first moveable structure for carrying, during use, a camera or lamp, the fluorometer being carried by a second moveable structure, wherein said at least one first moveable structure and said second moveable structure are coupled electrically and/or mechanically so that the movement of the second structure is synchronised with the movement of said at least one first structure.

28. A fluorometer as claimed in claim 1, wherein said excitation system is arranged such that said beam is capable of causing fluorescence in fluorescent material at distances of up to several meters from the fluorometer.

29. A fluorometer as claimed in claim 28, wherein said excitation system is arranged such that said beam is capable of causing fluorescence in fluorescent material at distances of between 1 and 15 meters from the fluorometer.

30. A fluorometer as claimed in claim 10, wherein the respective housings have a respective longitudinal axis, said longitudinal axes being substantially parallel with one another, and said generally conical divergent beam and said generally conical convergent detection volume are substantially aligned with said respective longitudinal axis.

31. A fluorometer as claimed in claim 1, wherein the generally conical divergent beam projecting from the fluorometer is non-scanned and diverges in a direction away from the fluorometer.

32. A fluorometer as claimed in claim 10, wherein the excitation system housing and the detection system housing each has a respective optical window through which said conical divergent beam and said received light, respectively, pass during use.

33. A fluorometer for detecting the level of fluorescent material in a body of water, the fluorometer comprising:
an excitation system including an excitation source for producing excitation light capable of causing fluorescence in fluorescent material; and
a detection system for detecting said fluorescence, wherein said excitation system comprises an excitation source comprising one or more light emitting diodes (LEDs), the excitation system further comprising means for causing said excitation light to form, in use, a generally conical divergent beam projecting from the fluorometer, said beam causing means comprising at least one collimating lens arranged to cause said excitation light to form a substantially collimated elongate beam that projects, during use, from the fluorometer, and said excitation system further including means for modulating said collimated elongate beam with a modulating signal having a modulating frequency, said excitation system being arranged such that said beam is capable of causing fluorescence in fluorescent material at distances of up to several meters from the fluorometer, and wherein
said detection system comprises means for receiving light and for converting said received light into a corresponding electrical signal, and at least one lens arranged to direct said received light onto said light receiving and converting means, wherein said at least one lens of the detection system is arranged to provide a generally conical convergent detection volume for the detection system, said generally conical detection volume converging in a direction towards said fluorometer and at least partially overlapping with said generally conical divergent beam, and wherein
said detection system further includes means for detecting, in the electrical signal produced by said light receiving and converting means, a signal component of substantially the same frequency as said modulation frequency, said detecting means including means for performing spectral analysis of said electrical signal and means for determining the value of a spectral component of said electrical signal corresponding to said modulation frequency, wherein said detection system is arranged to determine the level of fluorescent material present in said body of water depending on said value of said spectral component such that the fluorometer is capable of detecting fluorescent material located remotely from the fluorometer at distances of up to several meters from the fluorometer in said body of water,
and wherein the excitation system and the detection system are each provided in a respective housing, the respective housings being located adjacent one another and arranged such that there is an overlap, during use, between said generally conical divergent beam emanating from the excitation system housing and said generally conical convergent detection volume of the detection system housing, and wherein the respective housings have a respective longitudinal axis, said longitudinal axes being substantially parallel with one another, and said generally conical divergent beam and said generally conical convergent detection volume are substantially aligned with said respective longitudinal axis.

34. A fluorometer as claimed in claim 33, wherein the respective housings are adjustably interconnected so that the relative angular disposition between the respective housings may be altered such that the distance of said overlap from said respective housings is altered.

35. A fluorometer as claimed in claim 33, wherein the generally conical divergent beam projecting from the fluorometer is non-scanned and diverges in a direction away from the fluorometer, and
    wherein the excitation system housing and the detection system housing each has a respective optical window through which said conical divergent beam and said received light, respectively, pass during use.

36. A method of determining the level of a fluorescent material in a body of water remotely from a fluorometer, the fluorometer comprising an excitation system including an excitation source for producing excitation light capable of causing fluorescence in fluorescent material; and a detection system for detecting said fluorescence, the method comprising:
    generating said excitation light using at least one light emitting diode (LED);
    causing said excitation light to project from said excitation system in a generally conical divergent beam;
    using at least one collimating lens to form said divergent beam;
    modulating said beam with a modulating signal having a modulating frequency;
    receiving light at said detection system and converting said received light into a corresponding electrical signal;
    using at least one lens to provide a generally conical convergent detection volume for the detection system, said generally conical detection volume to converging in a direction towards said fluorometer;
    causing said generally conical detection volume to at least partially overlap with said generally conical divergent beam;
    detecting, in said electrical signal, a signal component of substantially the same frequency as said modulation frequency;
    determining the value of a spectral component of said electrical signal corresponding to said modulation frequency; and
    determining the level of fluorescent material present in said body of water depending on said value of said spectral component.

37. A fluorometer as claimed in claim 36, wherein the generally conical divergent beam projecting from the fluorometer is non-scanned and diverges in a direction away from the fluorometer.

\* \* \* \* \*